(12) United States Patent
Okuda et al.

(10) Patent No.: US 9,463,606 B2
(45) Date of Patent: Oct. 11, 2016

(54) COMPOSITE STRETCHABLE MEMBER
(71) Applicant: UNICHARM CORPORATION, Shikokuchuo-shi, Ehime (JP)
(72) Inventors: Jun Okuda, Kanonji (JP); Satoshi Mitsuno, Kanonji (JP); Noritomo Kameda, Kanonji (JP)
(73) Assignee: UNICHARM CORPORATION, Ehime (JP)
( * ) Notice: Subject to any disclaimer, the term of this patent is extended or adjusted under 35 U.S.C. 154(b) by 5 days.
(21) Appl. No.: 14/399,691
(22) PCT Filed: May 7, 2013
(86) PCT No.: PCT/JP2013/062834
§ 371 (c)(1),
(2) Date: Nov. 7, 2014
(87) PCT Pub. No.: WO2013/168701
PCT Pub. Date: Nov. 14, 2013
(65) Prior Publication Data
US 2015/0140278 A1 May 21, 2015
(30) Foreign Application Priority Data May 9, 2012 (JP) ................................. 2012-107768
May 9, 2012 (JP) ................................. 2012-107805

(51) Int. Cl.
B32B 5/02 (2006.01)
B32B 5/26 (2006.01)
(Continued)
(52) U.S. Cl.
CPC ............ B32B 5/022 (2013.01); *A61F 13/4902*
(2013.01); *B32B 3/18* (2013.01);
(Continued)
(58) Field of Classification Search
CPC ............ B32B 5/26; B32B 5/022; B32B 7/12; B32B 7/045; B32B 3/18; B32B 3/28; B32B 5/04; B32B 2250/20; B32B 2262/0207; B32B 2555/02; A61F 13/15; A61F 13/4902; Y10T 428/24041; Y10T 428/24058; Y10T 428/24686; Y10T 428/60; Y10T 428/601; Y10T 428/602; Y10T 428/659
USPC .................. 428/174, 181; 442/327, 328, 381
See application file for complete search history.

(56) References Cited

U.S. PATENT DOCUMENTS 4,626,305 A 12/1986 Suzuki et al.
5,340,648 A 8/1994 Rollins et al.
(Continued)

FOREIGN PATENT DOCUMENTS

EP 0556749 A1 8/1993
EP 2767267 A1 8/2014
(Continued)

OTHER PUBLICATIONS

International Search Report mailed Aug. 13, 2013, corresponding to International Application No. PCT/JP2013/062834, 2 pages.

Primary Examiner — Catherine A Simone
(74) Attorney, Agent, or Firm — Hauptman Ham, LLP

(57) ABSTRACT

Provided is a composite stretchable member with a smaller thickness and more uniform pleats. The composite stretchable member is stretchable in a first direction and is provided with a first nonwoven fabric sheet part and a second nonwoven fabric sheet part which are superposed on each other, and a plurality of elastic members which are arranged between the first nonwoven fabric sheet part and the second nonwoven fabric sheet part. The elastic members extend in the first direction while being separated from each other in a second direction perpendicular to the first direction, and the first nonwoven fabric sheet part and the second nonwoven fabric sheet part are joined with each other by an adhesive which is applied to the elastic members.

16 Claims, 12 Drawing Sheets

(51) Int. Cl.
  *B32B 7/12* (2006.01)
  *A61F 13/49* (2006.01)
  *B32B 3/28* (2006.01)
  *B32B 3/18* (2006.01)
  *B32B 7/04* (2006.01)

(52) U.S. Cl.
  CPC .......... *B32B 3/28* (2013.01); *B32B 5/26* (2013.01); *B32B 7/045* (2013.01); *B32B 7/12* (2013.01); *A61F 2013/49025* (2013.01); *B32B 2250/02* (2013.01); *B32B 2250/20* (2013.01); *B32B 2262/0292* (2013.01); *B32B 2305/20* (2013.01); *B32B 2307/51* (2013.01); *B32B 2555/02* (2013.01); *Y10T 428/24628* (2015.01); *Y10T 442/601* (2015.04)

(56) References Cited

U.S. PATENT DOCUMENTS

| | | |
|---|---|---|
| 2001/0056268 A1 | 12/2001 | Mizutani et al. |
| 2002/0148550 A1 | 10/2002 | Suzuki |
| 2003/0173018 A1 | 9/2003 | Harris |
| 2004/0015146 A1 | 1/2004 | Torigoshi et al. |
| 2006/0270302 A1 | 11/2006 | Ando et al. |
| 2008/0027406 A1 | 1/2008 | Shirai et al. |
| 2012/0095429 A1 | 4/2012 | Kobayashi et al. |

FOREIGN PATENT DOCUMENTS

| | | |
|---|---|---|
| JP | S58-180601 A | 10/1983 |
| JP | S63-21905 A | 1/1988 |
| JP | H05-140511 A | 6/1993 |
| JP | 2002-000653 A | 1/2002 |
| JP | 2002-172134 A | 6/2002 |
| JP | 2002-325793 A | 11/2002 |
| JP | 2003-153946 A | 5/2003 |
| JP | 2003-265520 A | 9/2003 |
| JP | 2003-328275 A | 11/2003 |
| JP | 2005-080859 A | 3/2005 |
| JP | 2006-149745 A | 6/2006 |
| JP | 2008-29836 A | 2/2008 |
| JP | 2008-029836 A | 2/2008 |
| JP | 2012-065849 A | 4/2012 |
| JP | 2013-081715 A | 5/2013 |
| WO | 95/34264 A1 | 12/1995 |
| WO | 2009/074922 A1 | 6/2009 |

(A)

(B)

COMPOSITE STRETCHABLE MEMBER

CROSS-REFERENCES TO RELATED APPLICATIONS

The present application is National Phase of International Application Number PCT/JP2013/062834 filed May 7, 2013 and claims the priority of Japanese patent Application No. 2012-107768 filed May 9, 2012 and of Japanese patent Application No. 2012-107805 filed May 9, 2012.

TECHNICAL FIELD

The present invention relates to a composite stretchable member.

BACKGROUND ART

Known in the art is a composite stretchable member which can stretch in a first direction (see PTL 1). This composite stretchable member is provided with a first nonwoven sheet and a second nonwoven sheet which are superposed on each other and a plurality of elastic members which are arranged between the first nonwoven sheet and the second nonwoven sheet. The first nonwoven sheet and the second nonwoven sheet are joined with each other at joined parts which are provided discontinuously in the first direction and a second direction which is perpendicular to the first direction. The elastic members extend in the first direction while separated from each other in the second direction without passing through the joined parts and are fastened to the first nonwoven sheet and the second nonwoven sheet at the two ends of the composite stretchable member in the first direction. As a result, in the contracted state, the first nonwoven sheet parts between two joined parts adjoining each other in the first direction deform in convex shapes outward in the thickness direction at one surface of the composite stretchable member, while the second nonwoven sheet parts between two joined parts adjoining each other in the first direction deform in convex shapes outward in the thickness direction at the other surface of the composite stretchable member. As a result, at one surface of the composite stretchable member, a large number of pleats are formed in the second direction by the first nonwoven sheet, while at the other surface of the composite stretchable member, a large number of pleats are formed in the second direction by the first nonwoven sheet.

CITATIONS LIST

Patent Literature

PTL 1: Japanese Patent Publication No. 2005-80859A

SUMMARY OF INVENTION

Technical Problem

The above-mentioned composite stretchable member is, for example, used for a member which contacts the skin of the wearer or is visible when worn such as a waist member which is positioned around the waist of the wearer of a disposable diaper.

In this case, from the viewpoint of contacting the skin of the wearer, the composite stretchable member preferably has a higher flexibility.

Further, if the composite stretchable member is high in heat retaining function, the temperature of the body surface of the wearer becomes higher and sweating or skin trouble is liable to occur. Therefore, the composite stretchable member is preferably low in heat retaining function. That is, the composite stretchable member is preferably small in thickness.

Furthermore, from the viewpoint of contacting the skin of the wearer, the composite stretchable member preferably has a more superior feeling. Furthermore, from the viewpoint of the visibility, the composite stretchable member preferably has a better look. That is, the pleats which are formed at the composite stretchable member are preferably smaller or more uniform.

In PTL 1, it may be considered that each first nonwoven sheet part between two joined parts which adjoin each other in the first direction forms a single pleat which is relatively higher, while each second nonwoven sheet part forms a single pleat which is relatively higher. However, it is difficult to form a single pleat between joined parts. In actually, a plurality of pleats which are relatively lower tend to be uniformly formed. That is, parts where the nonwoven sheet is superposed in multiple folds are liable to be formed at the composite stretchable member. Those parts are inferior in flexibility, so it is difficult to obtain uniformly excellent flexibility.

Further, the thickness of the composite stretchable member which is described in PTL 1, generally speaking, corresponds to the total of the height of the pleats which are formed by the first nonwoven sheet at one surface of the composite stretchable member and the height of the pleats which are formed by the second nonwoven sheet at the other surface of the composite stretchable member. Therefore, it is difficult to reduce the thickness of this composite stretchable member. Further, due to the pleats, an air layer is formed between the first nonwoven sheet and the second nonwoven sheet, so the heat retaining function of the composite stretchable member is increased and sweating etc. are liable to easily occur.

Furthermore, in PTL 1, it is considered that the first nonwoven sheet part between two joined parts adjoining each other in the first direction forms a single pleat and the second nonwoven sheet part forms a single pleat. However, it is difficult to form a single pleat between joined parts. In actuality, a plurality of pleats tend to be formed unevenly. That is, it is difficult for uniform pleats to be formed.

On this point, if reducing the intervals between the joined parts in the first direction, uniform pleats may be formed. However, if reducing the intervals, the area and number of joined parts per unit area of the composite stretchable member become greater and the composite stretchable member is liable to fall in flexibility. If reducing the areas of the individual joined parts to suppress a fall in flexibility, the first nonwoven sheet and the second nonwoven sheet will easily peel off from each other.

Solution to Problem

According to a first aspect of the present invention, there is provided a composite stretchable member which can stretch in a first direction, the composite stretchable member comprising a first nonwoven sheet part and a second nonwoven sheet part which are superposed each other and a plurality of elastic members which are arranged between the first nonwoven sheet part and the second nonwoven sheet part, the elastic members extending in the first direction while being separated from each other in a second direction perpendicular to the first direction, the first nonwoven sheet part and the second nonwoven sheet part joined with each other by an adhesive which is applied to the elastic members.

According to a second aspect of the present invention, there is provided a composite stretchable member which can stretch in a first direction, the composite stretchable member comprising a first nonwoven sheet part and a second nonwoven sheet part which are superposed each other and a plurality of elastic members which are arranged between the first nonwoven sheet part and the second nonwoven sheet part, the elastic members extending in the first direction while being separated from each other in a second direction perpendicular to the first direction, the first nonwoven sheet part and the second nonwoven sheet part joined with each other by an adhesive which is applied to the elastic members, a thickness when applying 3 $gf/cm^2$ of pressure in the thickness direction to the composite stretchable member in a 50% stretched state being 2.0 mm or less, and a root mean square height of a profile curve in a 50% stretched state being 0.4 mm or less.

According to a third aspect of the present invention, there is provided a composite stretchable member which can stretch in a first direction, the composite stretchable member comprising a first nonwoven sheet part and a second nonwoven sheet part which are superposed each other and a plurality of elastic members which are arranged between the first nonwoven sheet part and the second nonwoven sheet part, the elastic members extending in the first direction while being separated from each other in a second direction perpendicular to the first direction, the first nonwoven sheet part and the second nonwoven sheet part joined with each other by an adhesive which is applied to the elastic members, and a coefficient of variation of length of profile curve elements in a 50% stretched state being 0.2 or less.

According to a fourth aspect of the present invention, there is provided a composite stretchable member which can stretch in a first direction, the composite stretchable member comprising a first nonwoven sheet part and second nonwoven sheet part which are superposed on each other and a plurality of elastic members which are arranged between the first nonwoven sheet part and the second nonwoven sheet part, the elastic members extending in the first direction while being separated from each other in a second direction perpendicular to the first direction, the first nonwoven sheet part and the second nonwoven sheet part joined with each other by an adhesive which is applied to the elastic members, and a heat retaining rate in a 50% stretched state being 40% or less.

According to a fifth aspect of the present invention, there is provided a composite elastic which can stretch in a first direction, the composite stretchable member comprising a first nonwoven sheet part and a second nonwoven sheet part which are superposed on each other and a plurality of elastic members which are arranged between the first nonwoven sheet part and the second nonwoven sheet part, the elastic members extending in the first direction while being separated from each other in a second direction perpendicular to the first direction, the first nonwoven sheet part and the second nonwoven sheet part joined with each other by an adhesive which is applied to the elastic members, and a density of profile curve elements in a 50% stretched state being 8 to 15/cm.

According to a sixth aspect of the present invention, there is provided a composite stretchable member which can stretch in a first direction, the composite stretchable member comprising a first nonwoven sheet part and a second nonwoven sheet part which are superposed on each other and a plurality of elastic members which are arranged between the first nonwoven sheet part and the second nonwoven sheet part, the elastic members extending in the first direction while being separated from each other in a second direction perpendicular to the first direction, the first nonwoven sheet part and the second nonwoven sheet part joined with each other by an adhesive which is applied to the elastic members, a mean compressive pressure when compressing the composite stretchable member in the thickness direction so that the load which is applied to the composite stretchable member in a 50% stretched state changes from 0.5 $gf/cm^2$ to 50 $gf/cm^2$ being less than 15 $gf/cm^2$, and a root mean square height of a profile curve in a 50% stretched state being 0.4 mm or less.

Advantageous Effects of Invention

It is possible to provide a composite stretchable member which can reliably maintain the bond between the first nonwoven sheet part and the second nonwoven sheet part while keeping the adhesive from causing the composite stretchable member to fall in flexibility.

It is possible to provide a composite stretchable member with a smaller thickness and more uniform pleats.

It is possible to provide a composite stretchable member with more uniformly excellent flexibility.

DESCRIPTION OF EMBODIMENTS

Figure 1:
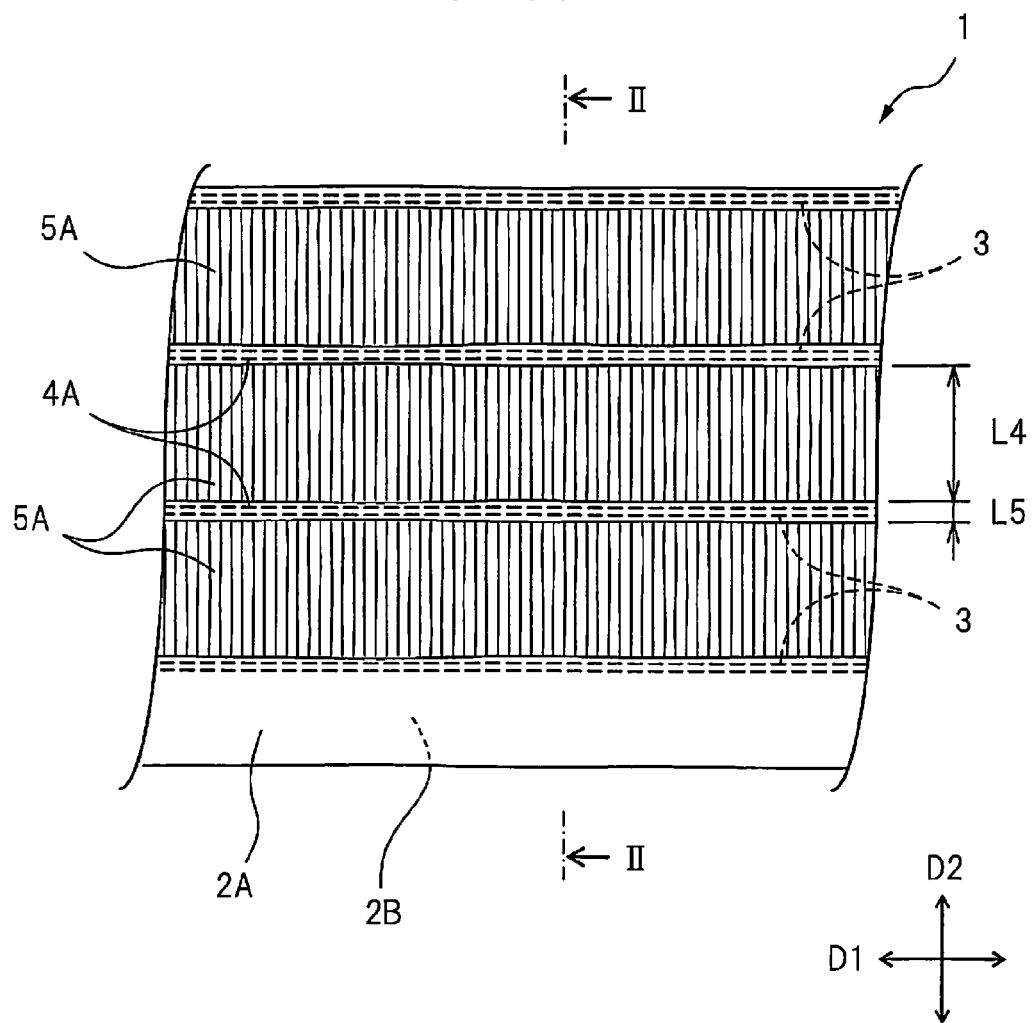
FIG. 1 is a partial plan view of a composite stretchable member of an embodiment according to the present invention.
Figure 2:
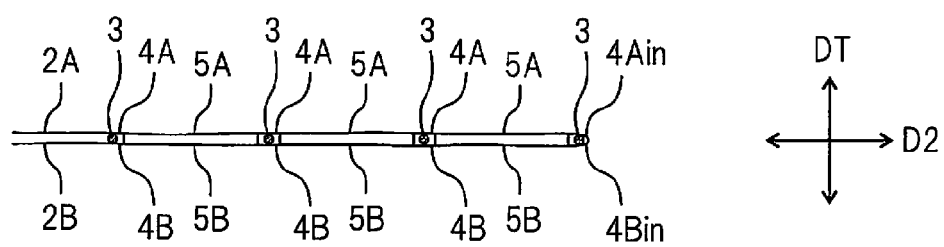
FIG. 2 is a cross-sectional view seen along a line II-II in FIG. 1.

FIG. 1 and FIG. 2 show a composite stretchable member 1 of an embodiment according to the present invention. This composite stretchable member 1 is used for producing an absorbent product such as a disposable diaper or sanitary napkin. In particular, the composite stretchable member 1 is used for a member which contacts the skin of a wearer or is visible when worn such as a waist member which is positioned around the waist of the wearer.

Referring to FIG. 1 and FIG. 2, the composite stretchable member 1 forms a sheet shape which extends in a first direction D1 and in a second direction D2 perpendicular to the first direction D1. The composite stretchable member 1 can stretch in the first direction D1, therefore the first direction D1 corresponds to the stretch direction of the composite stretchable member 1. FIG. 1 shows the state where the composite stretchable member 1 is stretched in the first direction D1. The composite stretchable member 1 is provided with a mutually superposed first nonwoven sheet part 2A and second nonwoven sheet part 2B and a plurality of, for example, four, elastic members 3 which are arranged between the first nonwoven sheet part 2A and the second nonwoven sheet part 2B. The elastic members 3 extend in the first direction D1 while separated from each other by equal intervals in the second direction D2.

Further, the first nonwoven sheet part 2A and the second nonwoven sheet part 2B are respectively provided with pluralities of convex-concave regions 5A, 5B and at least one non-shaped regions 4A, 4B which separate these convex-concave regions 5A, 5B from each other in the second direction D2. In the embodiment shown in FIG. 1 and FIG. 2, three convex-concave regions 5A, 5B and four non-shaped regions 4A, 4B are provided. The length L4 of the non-shaped regions 4A, 4B in the second direction D2 is, for example, about 1 mm, while the length L5 of the convex-concave regions 5A, 5B in the second direction D2 is, for example, about 4 mm.

Figure 3:
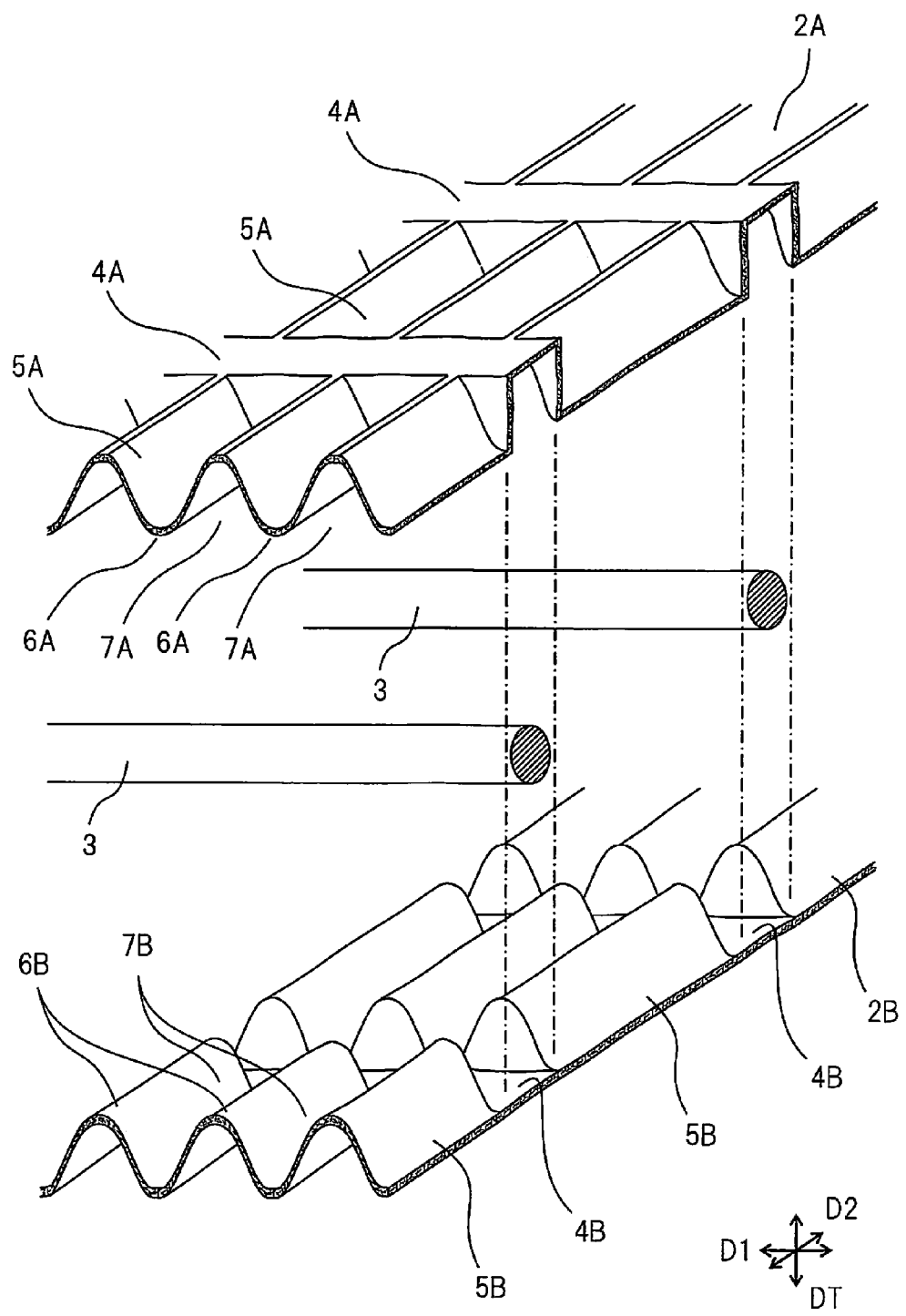
FIG. 3 is a partial exploded perspective view of the composite stretchable member.

As shown in FIG. 3, the convex-concave regions 5A of the first nonwoven sheet part 2A are provided with convex parts 6A and concave parts 7A which are alternately repeated in the first direction D1 and which continue in the second direction D2. The convex parts 6A respectively stick out from the non-shaped regions 4A in the thickness direction DT. The concave parts 7A respectively reach the non-shaped regions 4A between two mutually adjoining convex parts 6A. The non-shaped regions 4A are not provided with convex parts and concave parts. Further, the non-shaped regions 4A are positioned at one surface of the first nonwoven sheet part 2A, in the embodiment shown in FIG. 3, at the top surface side, while the convex-concave regions 5A are positioned at the other surface of the first nonwoven sheet part 2A, in the embodiment shown in FIG. 3, at the bottom surface side.

Similarly, the convex-concave regions 5B of the second nonwoven sheet part 2B are provided with convex parts 6B and concave parts 7B which are alternately repeated in the first direction D1 and which continue in the second direction D2. The convex parts 6B respectively stick out from the non-shaped regions 4B in the thickness direction DT. The concave parts 7B respectively reach the non-shaped regions 4B between two mutually adjoining convex parts 6B. The non-shaped regions 4B are not provided with convex parts and concave parts. Further, the non-shaped regions 4B are positioned at one surface of the second nonwoven sheet part 2B, in the embodiment shown in FIG. 3, at the bottom surface side, while the convex-concave regions 5B are positioned at the other surface of the second nonwoven sheet part 2B, in the embodiment shown in FIG. 3, at the top surface side.

If considering that the non-shaped regions 4A, 4B respectively extend in a virtual reference plane, the convex parts 6A, 6B stick out from the corresponding reference plane, while the concave parts 7A, 7B reach the corresponding reference plane. Note that, the first nonwoven sheet part 2A and the second nonwoven sheet part 2B is flexible, so the reference plane is not necessarily a flat plane.

Figure 4:
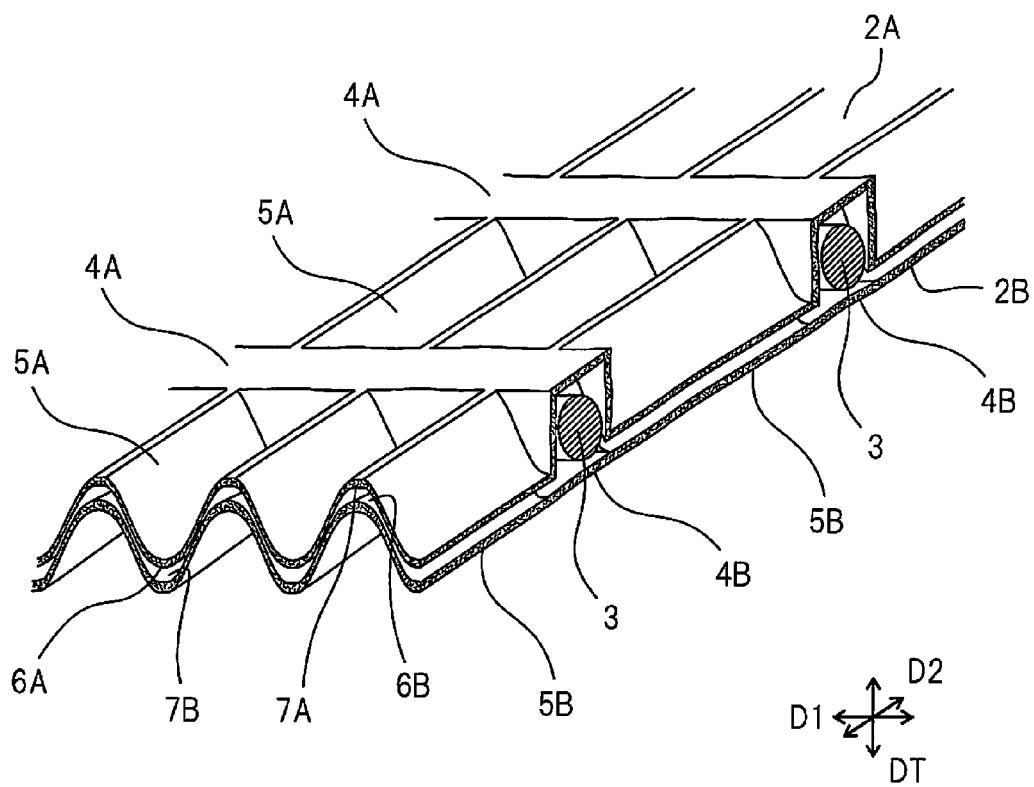
FIG. 4 is a partial cross-sectional perspective view of the composite stretchable member.

Moreover, as shown in FIG. 4, the first nonwoven sheet part 2A and the second nonwoven sheet part 2B are superposed so that the convex-concave regions 5A, 5B adjoin each other and the non-shaped regions 4A, 4B are separated from each other. In this case, in the second direction D2, the convex-concave regions 5A, 5B are aligned with each other and the non-shaped regions 4A, 4B are aligned with each other. Further, in the first direction D1, the convex parts 6A of the first nonwoven sheet part 2A respectively face the concave parts 7B of the second nonwoven sheet part 2B, while the convex parts 6B of the second nonwoven sheet part 2B respectively face the concave parts 7A of the first nonwoven sheet part 2A. As a result, the convex parts 6A of the first nonwoven sheet part 2A at least partly enter into the concave parts 7B of the second nonwoven sheet part 2B, while the convex parts 6B of the second nonwoven sheet part 2B at least partly enter into the concave parts 7A of the first nonwoven sheet part 2A.

Figure 5:
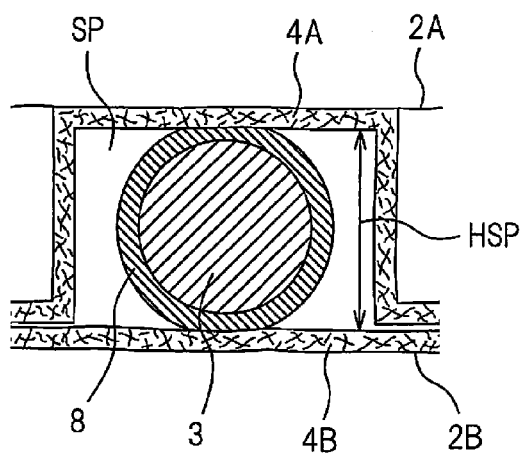
FIG. 5 is a partial cross-sectional view of a composite stretchable member.

As explained above, the non-shaped regions 4A, 4B are separated from each other in the thickness direction DT. Therefore, as shown in FIG. 5, spaces SP are formed between the mutually facing non-shaped regions 4A, 4B, and elastic members 3 are arranged in the spaces SP. An adhesive 8 is applied in advance to the circumferential surfaces of the elastic members 3. By the adhesive 8, the first nonwoven sheet part 2A and the second nonwoven sheet part 2B are joined together. In another embodiment, the adhesive 8 is partially applied to the circumferential surfaces of the elastic members 3.

In other words, the first nonwoven sheet part 2A and the second nonwoven sheet part 2B are indirectly joined via the elastic members 3. Further, there is no adhesive at the convex-concave regions 5A, 5B, therefore the first nonwoven sheet part 2A and the second nonwoven sheet part 2B are not directly joined. By doing this, the bond between the first nonwoven sheet part 2A and the second nonwoven sheet part 2B is reliably maintained while the composite stretchable member 1 is kept from falling in flexibility due to the adhesive.

As a result, the composite stretchable member 1 is given stretch properties in the first direction D1. Further, the composite stretchable member 1 is formed with a large number of pleats which are continuous in the second direction D2 due to the convex parts 6A, 6B and concave parts 7A, 7B.

The first nonwoven sheet part 2A and the second nonwoven sheet part 2B at the non-shaped regions 4A, 4B may include parts which are not joined to the elastic members 3. In this case, at the time of contraction of the composite stretchable member 1, the above parts may rise up. Further, in the non-shaped regions 4A, 4B, at the outside surfaces of the first nonwoven sheet part 2A and the second nonwoven sheet part 2B, i.e., at the surfaces of the opposite sides to the elastic members 3, compared with the inside surfaces of the first nonwoven sheet part 2A and the second nonwoven sheet part 2B, i.e., the surfaces facing the elastic members 3, the fibers which form the nonwoven sheets are relatively free. For this reason, at the time of contraction of the composite stretchable member 1, the fibers at the above outside surfaces may rise up. As a result, in each case, at the time of contraction of the composite stretchable member 1, pleats are formed extending from single convex-concave region 5A, 5B to other convex-concave regions 5A, 5B across the non-shaped regions 4A, 4B.

The diameters of the elastic members 3 are preferably slightly smaller than the heights HSP of the spaces SP. This is because if the diameters of the elastic members 3 are larger than the heights HSP, the elastic members 3 or cured adhesive 8 will stick out at the non-shaped regions 4A, 4B in the thickness direction DT and the wearer is liable to be given an odd feeling.

Figure 6:
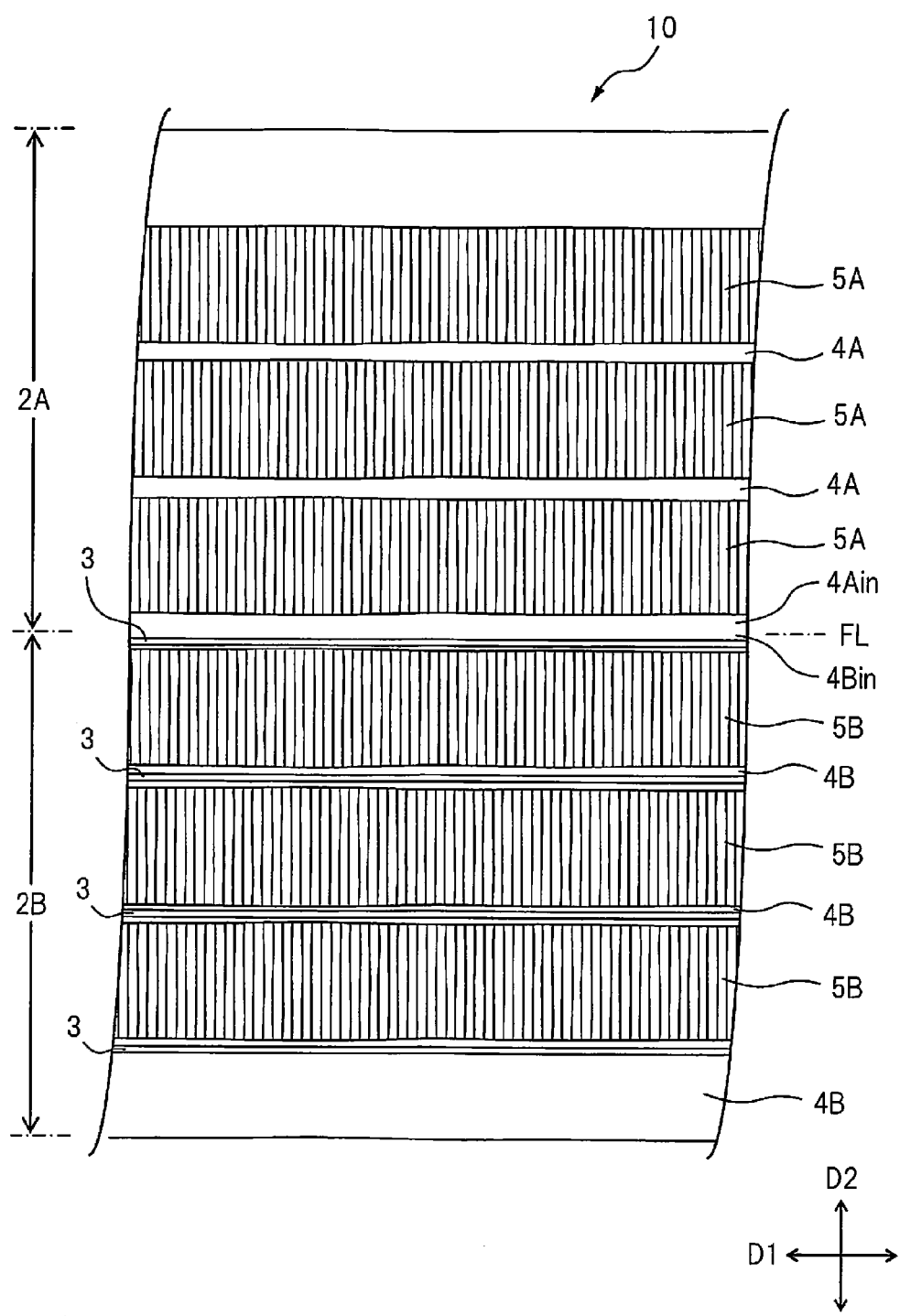
FIG. 6 is a partial laid open view of the composite stretchable member.

As shown in FIG. 6, the first nonwoven sheet part 2A and the second nonwoven sheet part 2B are formed in the same nonwoven sheet 10. That is, the nonwoven sheet 10 has a folding line FL which extends in the first direction D1. At one side of the folding line FL, the first nonwoven sheet part 2A is formed, while at the other side of the folding line FL, the second nonwoven sheet part 2B is formed. If calling the non-shaped regions 4A, 4B of the first nonwoven sheet part 2A and the second nonwoven sheet part 2B which adjoin the folding line FL the innermost non-shaped regions 4Ain, 4Bin, these innermost non-shaped regions 4Ain, 4Bin are connected with each other.

Further, the non-shaped regions 4A of the first nonwoven sheet part 2A and the non-shaped regions 4B of the second nonwoven sheet part 2B are positioned on the same surface of the nonwoven sheet 10, in the embodiment shown in FIG. 6, at the bottom surface side. As opposed to this, the convex-concave regions 5A of the first nonwoven sheet part 2A and the convex-concave regions 5B of the second nonwoven sheet part 2B are positioned on the same surface of the nonwoven sheet 10, in the embodiment shown in FIG. 6, at the top surface side.

Figure 7:
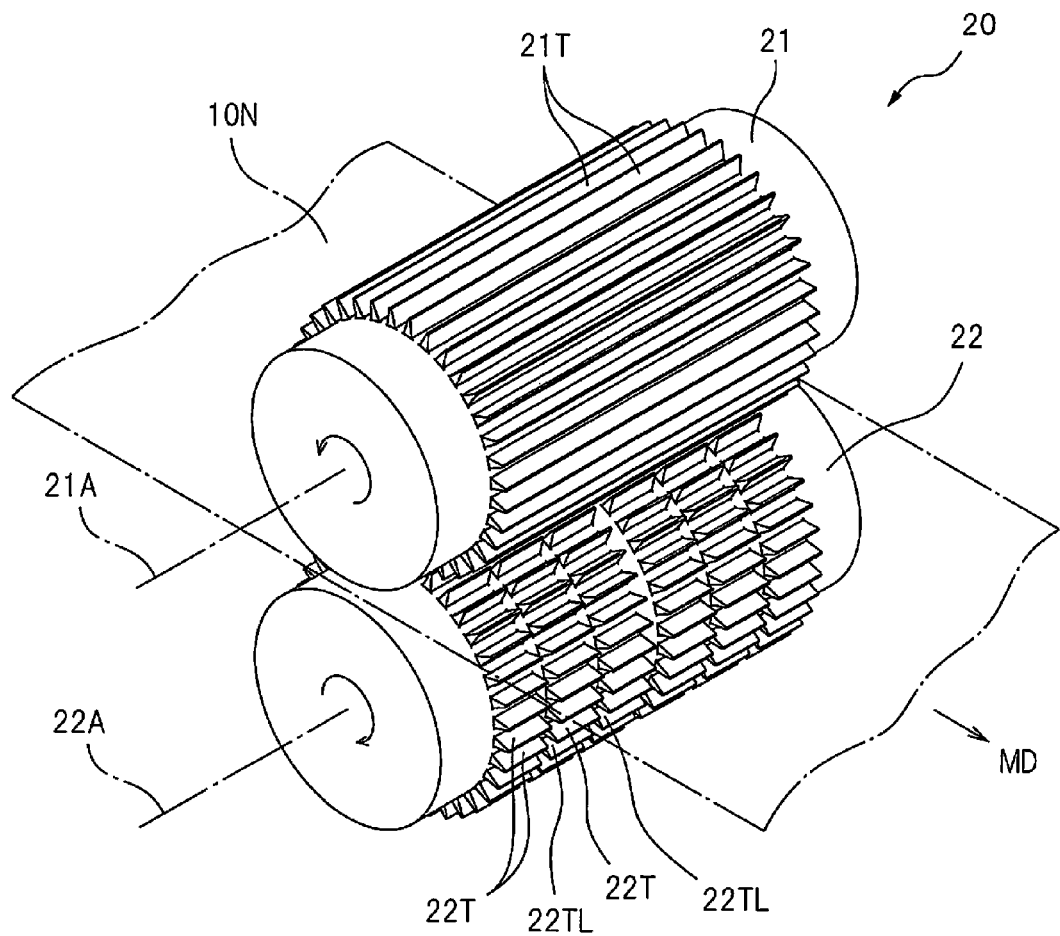
FIG. 7 is a schematic view of a shaping device.

The non-shaped regions 4A, 4B and convex-concave regions 5A, 5B are, for example, formed by a shaping device 20 shown in FIG. 7. That is, the shaping device 20 is provided with a pair of a continuous gear roll 21 and discontinuous gear roll 22 which can rotate about mutually parallel rotational axes 21A, 22A in opposite directions while intermeshing each other. The continuous gear roll 21 is provided with a plurality of teeth 21T which extend continuously along the rotational axis 21A. As opposed to this, the discontinuous gear roll 22 is provided with a plurality of teeth 22T which extend discontinuously along the rotational axis 22A. That is, the teeth 22T are separated from each other by discontinuous parts 22TL in the rotational axis 22A direction.

A not yet shaped nonwoven sheet 10N is passed between these continuous gear roll 21 and discontinuous gear roll 22. In this case, the machine direction MD of the nonwoven sheet 10N corresponds to the first direction D1, while the rotational axis 21A, 22A directions of the continuous gear roll 21 and discontinuous gear roll 22 correspond to the second direction D2. As a result, in the region where the teeth 21T of the continuous gear roll 21 and the teeth 22T of the discontinuous gear roll 22 face each other, the nonwoven sheet 10N is partially stretched, that is, is shaped, along the first direction D1. As a result, convex parts 6A, 6B and concave parts 7A, 7B are alternately repeatedly formed. That is, convex-concave regions 5A, 5B are formed. On the other hand, in the region where the teeth 21T of the continuous gear roll 21 and the discontinuous parts 22TL of the discontinuous gear roll 22 face each other, convex parts and concave parts are not formed, therefore non-shaped regions 4A, 4B are formed. In this way, a single shaping treatment enables the first nonwoven sheet part 2A and the second nonwoven sheet part 2B to be simultaneously formed. In another embodiment, the first nonwoven sheet part 2A and the second nonwoven sheet part 2B are formed in different nonwoven sheets and are superposed with each other.

Note that, if the above-mentioned such shaping treatment by stretching is performed, the distances between fibers increases at the intermediate parts between the convex parts 6A, 6B and the concave parts 7A, 7B, so the strength of the intermediate parts is weakened. As a result, the nonwoven sheet is increased in flexibility.

Next, while the nonwoven sheet 10 is conveyed, the elastic members 3 are adhered to the nonwoven sheet 10. Specifically, the elastic members 3 to which the adhesive 8 has been applied in advance are arranged in a stretched state at, for example, the non-shaped regions 4B of the second nonwoven sheet part 2B. In this case, the stretch-bond ratio of the elastic members 3 (=(length of elastic member 3 in stretched state adhered to nonwoven fabric sheet 10 with a unit length in the machine direction MD)/(length of elastic member 3 in contracted state)) is, for example, set to 3.

Next, while the nonwoven sheet 10 is conveyed, it is folded generally along the folding line FL shown in FIG. 6. Due to this, the first nonwoven sheet part 2A and the second nonwoven sheet part 2B are superposed. Next, the composite stretchable member 1 is pressed, for example by a press roller, in the thickness direction DT. As a result, the convex parts 6A of the first nonwoven sheet part 2A at least partially enter into the concave parts 7B of the second nonwoven sheet part 2B, while the convex parts 6B of the second nonwoven sheet part 2B at least partially enter into the concave parts 7A of the first nonwoven sheet part 2A. Further, by the adhesive 8 (FIG. 5) which is applied to the elastic members 3, the first nonwoven sheet part 2A and the second nonwoven sheet part 2B are joined with each other. In this way, the composite stretchable member 1 is formed.

Note that, when folding the nonwoven sheet 10 generally along the folding line FL, one of the first nonwoven sheet part 2A and the second nonwoven sheet part 2B is moved slightly in the first direction D1 with respect to the other so that the convex parts 6A of the first nonwoven sheet part 2A face the concave parts 7B of the second nonwoven sheet part 2B and the convex parts 6B of the second nonwoven sheet part 2B face the concave parts 7A of the first nonwoven sheet part 2A. This movement can be obtained, for example by making the tensions of the first nonwoven sheet part 2A and the second nonwoven sheet part 2B at the time of conveyance different.

Figure 8:
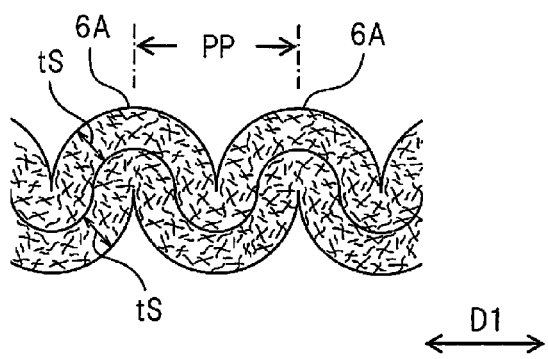
FIG. 8 is a schematic cross-sectional view of convex-concave regions of a composite stretchable member in a contracted state.

As explained above, the convex parts 6A of the first nonwoven sheet part 2A enter into the concave parts 7B of the second nonwoven sheet part 2B, and the convex parts 6B of the second nonwoven sheet part 2B enter into the concave parts 7A of the first nonwoven sheet part 2A. To achieve this, as will be understood from FIG. 8, the pitch PP of the convex parts 6A, 6B or concave parts 7A, 7B at the composite stretchable member 1 in the contracted state or natural state has to be set to at least a thickness of the amount of four nonwoven sheet parts 4. On the other hand, the state of the nonwoven sheet 10 when shaping treatment is performed, that is, before the elastic members 3 are adhered, corresponds to the state of the first nonwoven sheet part 2A and the second nonwoven sheet part 2B when stretching the composite stretchable member 1 to the maximum extent in the first direction D1. Therefore, when expressing the maximum stretch ratio in the first direction of the composite stretchable member 1 by ERM, the pitch PP0 of the convex parts 6A, 6B or concave parts 7A, 7B at the nonwoven sheet 10 before the elastic members 3 is adhered expressed by PP·ERM. Further, when expressing the thickness of the nonwoven sheet 10 before the shaping treatment as tS0 and the extension ratio of the shaping device 20 (=length of path of nonwoven sheet part after shaping treatment/length of path of nonwoven sheet part before shaping treatment) as DR, the thickness tS of the nonwoven sheet 10 after shaping treatment is expressed by tS0/DR. This being so, the pitch PP0 has to satisfy the following formula (1).

$$PP0 \geq 4 \cdot tS \cdot ERM = 4 \cdot (tS0/DR) \cdot ERM \quad (1)$$

Therefore, the pitch PP0 is determined from the predetermined tS0, DR and ERM so as to satisfy formula (1).

In the embodiment shown in FIG. 1 and FIG. 2, the first nonwoven sheet part 2A and the second nonwoven sheet part 2B are formed from a spun-bond nonwoven fabric with a basis weight of 17 g/m². In another embodiment, the first nonwoven sheet part 2A and the second nonwoven sheet part 2B are, for example, formed from a melt blown nonwoven fabric, SMS nonwoven fabric by the combination of a spun-bond nonwoven fabric and a melt blown nonwoven fabric, heat roll nonwoven fabric, air-through nonwoven fabric, spun-lace nonwoven fabric, air-laid nonwoven fabric, etc. The nonwoven fabric is made of polyethylene, polypropylene, polyester, acryl, etc.

Further, in the embodiment shown in FIG. 1 and FIG. 2, the elastic members 3 are formed from Lycra® with a denier of 470 dtex. In another embodiment, they are made of styrene-butadiene, butadiene, isoprene, neoprene, or another, natural rubber, EVA, SIS, SEGS, SEPS, stretch polyolefin, polyurethane, etc. The denier of the elastic member 3 is preferably 30 to 1500 dtex. In another embodiment, one or both of the material and denier of the elastic members 3 differ.

Furthermore, in the embodiment shown in FIG. 1 and FIG. 2, the non-shaped regions 4A, 4B are formed at equal intervals in the second direction D2, therefore the elastic members 3 are arranged at equal intervals in the second direction D2. In another embodiment, the non-shaped regions 4A, 4B are formed at unequal intervals in the second direction D2, so the elastic members 3 are arranged at unequal intervals in the second direction D2.

Figure 9:
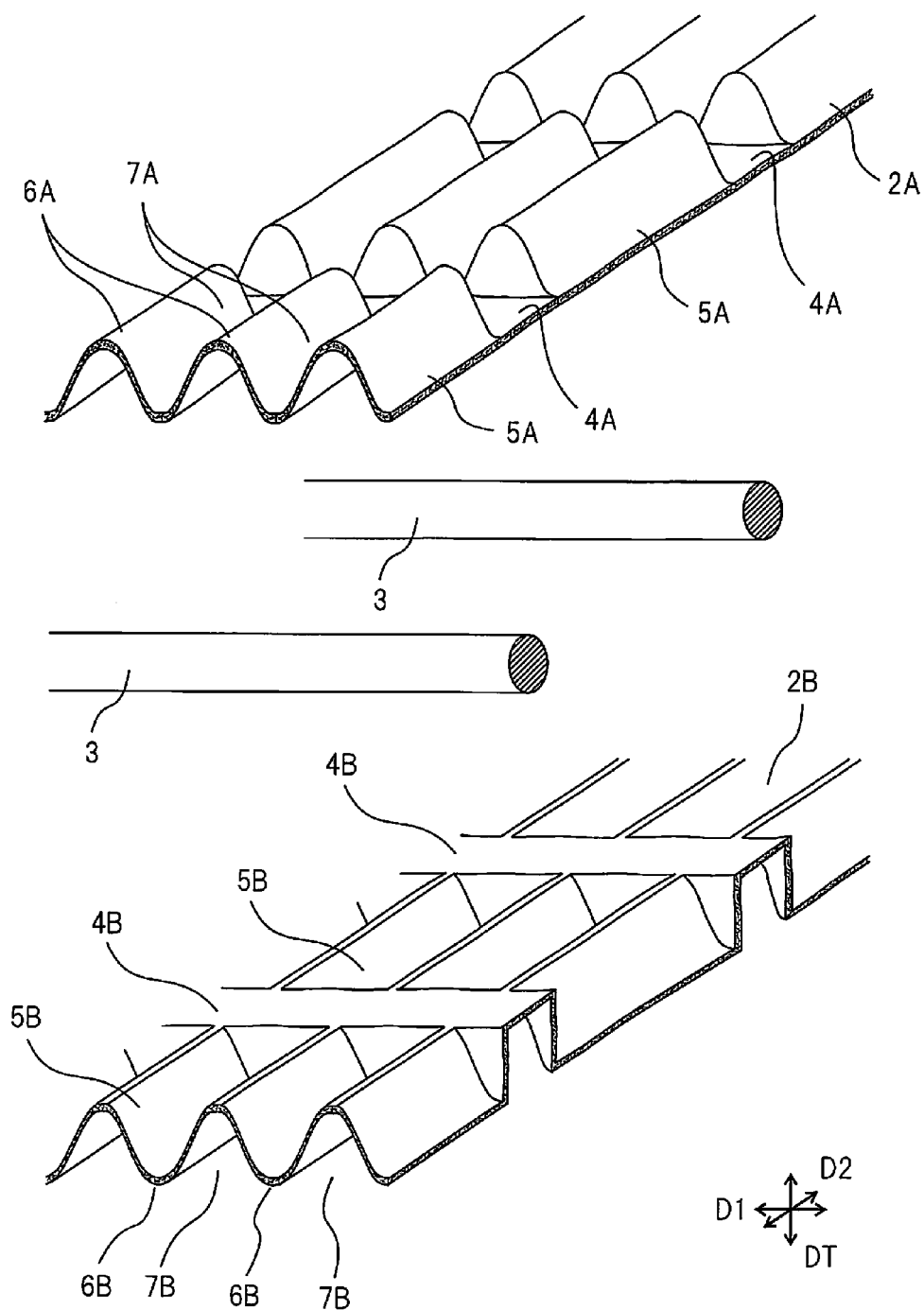
FIG. 9 is a partial exploded perspective view of another embodiment according to the present invention.

FIG. 9 shows another embodiment according to the present invention. In the embodiment shown in FIG. 9 as well, the composite stretchable member 1 is formed from the nonwoven sheet 10 shown in FIG. 6. However, the first nonwoven sheet part 2A and the second nonwoven sheet part 2B are superposed so that the convex-concave regions 5A, 5B are separated from each other and the non-shaped regions 4A, 4B adjoin each other. In this case, in the second direction D2, the convex-concave regions 5A, 5B are aligned with each other, and the non-shaped regions 4A, 4B are aligned with each other. Furthermore, the elastic members 3 are arranged at equal intervals in the second direction D2 between the first nonwoven sheet part 2A and the second nonwoven sheet part 2B, and the first nonwoven sheet part 2A and the second nonwoven sheet part 2B are joined via the elastic members 3. In this case, the elastic members 3 are preferably arranged between the non-shaped regions 4A, 4B. In another embodiment, in the second direction D2, the first nonwoven sheet part 2A and the second nonwoven sheet part 2B are superposed so that the convex-concave regions 5A, 5B are not aligned with each other and the non-shaped regions 4A, 4B are not aligned with each other. In still another embodiment, the elastic members 3 are arranged at unequal intervals in the second direction D2.

The composite stretchable member according to a first aspect of the present invention is a composite stretchable member which can stretch in a first direction, comprised of a first nonwoven sheet part and a second nonwoven sheet part which are superposed on each other and a plurality of elastic members which are arranged between the first nonwoven sheet part and the second nonwoven sheet part, the elastic members extending in the first direction while being separated from each other in a second direction which is perpendicular to the first direction, the first nonwoven sheet part and the second nonwoven sheet part joined with each other by an adhesive which is applied to the elastic members.

Now, a composite stretchable member according to a second aspect of the present invention has a thickness 5 when applying 3 gf/cm² (0.3 kPa) of pressure in the thickness direction to the composite stretchable member in a 50% stretched state of 2.0 mm or less and has a root mean square height Pq of a profile curve in a 50% stretched state of 0.4 mm or less.

The composite stretchable member according to the second aspect of the present invention preferably further has a coefficient of variation CV of the length of the profile curve element in a 50% stretched state of 0.2 or less.

The composite stretchable member according to the second aspect of the present invention preferably further has a mean compressive pressure CP, when compressing the composite stretchable member in the thickness direction so that the load which is applied to the composite stretchable member in a 50% stretched state changes from 0.5 gf/cm² (0.05 kPa) to 50 gf/cm² (5 kPa), of less than 15 gf/cm² (1.5 kPa).

The composite stretchable member according to the second aspect of the present invention preferably further has a heat retaining rate HR in a 50% stretched state of 40% or less.

The composite stretchable member according to the second aspect of the present invention preferably further has a density D of the profile curve elements in a 50% stretched state of 8 to 15/cm.

The 50% stretched state is the state where the composite stretchable member is stretched in the stretch direction so that the stretch ratio becomes 50%. The stretch ratio is defined by the following formula:

$$\text{Stretch ratio (\%)} = (LM - LM0)/LM0 \cdot 100$$

Figure 10:
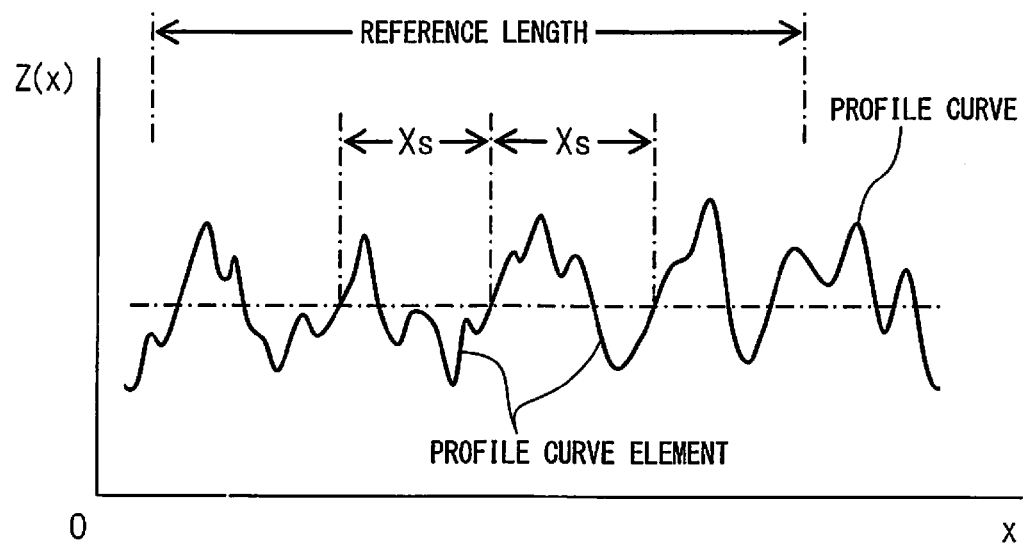
FIG. 10 is a graph which explains the height and length of a cross-sectional curvature element.

Here, LM: stretch direction length of stretched composite stretchable member part LM0: stretch direction length of the composite stretchable member part in natural state The thickness t is measured by a thickness measuring device. On the other hand, the root mean square height Pq of the profile curve is found as follows: That is, first, the profile curve along the stretch direction at the convex-concave regions of the composite stretchable member is measured by a shape measuring device. The cross-sectional shape is preferably measured at the substantial center of two mutually adjoining elastic members. Next, from this profile curve, the height Z(x) of the profile curve element at the reference length is found (see FIG. 10). Next, the root mean square height Pq of the profile curve is calculated from the height Z(x) of the profile curve element (see JIS B 0601: 2001 (ISO4287: 1997), JIS B 0651: 2001 (ISO3274: 1996)). The x-axial direction corresponds to the stretch direction.

The root mean square height Pq of the profile curve expresses the size of the pleats or uniformity of the pleats formed at the composite stretchable member. Specifically, as the root mean square height Pq becomes smaller, the pleats become smaller and more uniform. Therefore, if the thickness t is 2.0 mm or less and the root mean square height Pq is 0.4 mm or less, a composite stretchable member with a smaller thickness and simultaneously more uniform pleats is provided. If the thickness is smaller, the composite stretchable member becomes lower in heat retaining function and sweating or skin trouble is suppressed. Further, the composite stretchable member is enhanced in flexibility. On the other hand, if the pleats are more uniform, the composite stretchable member is improved in feeling and look. Further, the uniformity of characteristics of the composite stretchable member such as the feel and flexibility is enhanced more.

The coefficient of variation CV of the length of the profile curve elements is found as follows: That is, the length Xs of the profile curve elements at the reference length is found from the above profile curve (see FIG. 10). Next, the arithmetic mean value PSm and standard deviation $\sigma$ of the length Xs of the profile curve elements are calculated. Next, the coefficient of variation CV of the length Xs of the profile curve elements is calculated (CV=$\sigma$/PSm).

The length Xs of the profile curve elements expresses the interval or size of the pleats of the composite stretchable member, while the coefficient of variation CV of the length Xs expresses the uniformity of pleats. Specifically, as the coefficient of variation CV becomes smaller, the pleats become more uniform. Therefore, if the coefficient of variation CV is 0.2 or less, a composite stretchable member with more uniform pleats is provided. In other words, a composite stretchable member with better feel and look is provided. Further, the uniformity of characteristics of the composite stretchable member such as touch and flexibility is enhanced more.

Figure 11:
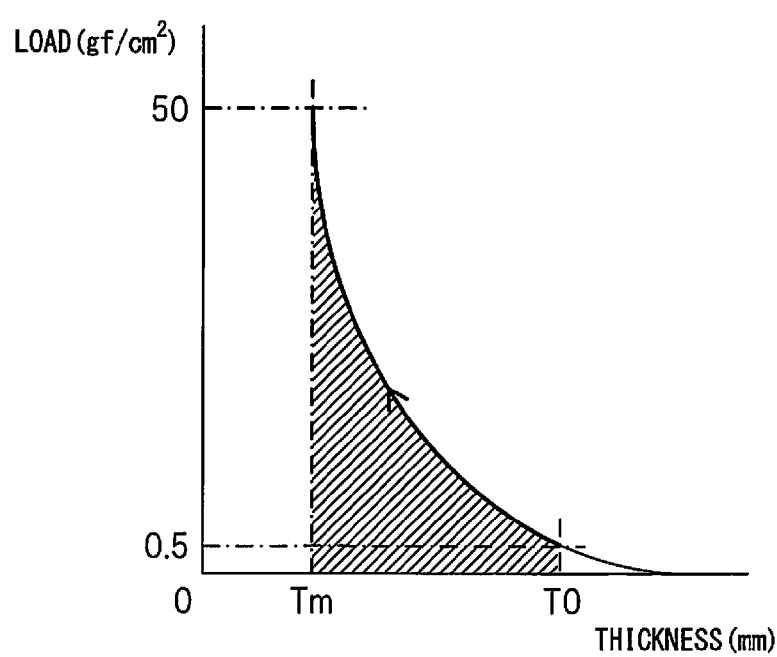
FIG. 11 is a graph which explains a method of calculation of a mean compressive pressure.

The mean compressive pressure CP is found as follows: That is, as shown in FIG. 11, the composite stretchable member is compressed in the thickness direction until the load which is applied to the composite stretchable member in a 50% stretched state changes from 0.5 gf/cm$^2$ to 50 gf/cm$^2$, and the amount of work WC which is required for this compression is measured. This amount of compression work WC corresponds to the area of the hatched region in FIG. 11. Further, the thickness TO of the composite stretchable member when the load applied to the compressed composite stretchable member is 0.5 gf/cm$^2$ and the thickness Tm of the composite stretchable member when the load applied to the composite stretchable member is 50 gf/cm$^2$ are measured. Next, from these WC, T0 and Tm, the mean compressive pressure CP is calculated (CP=WC/(Tm−T0)).

The mean compressive pressure CP expresses the flexibility of the composite stretchable member. Specifically, as the mean compressive pressure CP becomes smaller, the composite stretchable member is improved in flexibility. Therefore, if the mean compressive pressure CP is less than 15 gf/cm$^2$, a composite stretchable member with better flexibility is provided. Further, if the mean compressive pressure CP is less than 15 gf/cm$^2$ and the root mean square height Pq is 0.4 mm or less, a better flexibility can uniformly obtained.

The heat retaining rate HR was found as follows: That is, first, a heated hot plate is prepared. Next, the quantity of heat Qd which is required for maintaining the temperature of the hot plate when arranging a composite stretchable member on the hot plate is measured. Further, the quantity of heat Q0 which is required for maintaining the temperature of the hot plate when not arranging a composite stretchable member on the hot plate is measured. Next, from these Qd, Q0, the heat retaining rate HR is calculated (HR(%)=(Q0−Qd)/Q0·100).

If the heat retaining rate HR is 40% or less, the temperature of the body surface of the wearer is maintained low and sweating or skin trouble is suppressed.

The density D of the profile curve elements is calculated from the mean value PSm of the length Xs of the profile curve elements (D=1/PSm).

The density D of the profile curve elements expresses the magnitude or uniformity of pleats of the composite stretchable member. Specifically, as the density D becomes larger, the pleats become smaller and become more uniform. Therefore, if the density D is 8 to 15/cm, a composite stretchable member with more uniform pleats is provided. In other words, a composite stretchable member with a better feel and look is provided. Further, the uniformity of characteristics of the composite stretchable member such as the feel and flexibility is enhanced more. Furthermore, the pleats are not excessively small, so production of the composite stretchable member is easy.

The composite stretchable member according to a third aspect of the present invention has a coefficient of variation CV of the length Xs of the profile curve elements of 0.2 or less. The composite stretchable member according to the third aspect of the present invention further preferably has a root mean square height Pq of 0.4 mm or less.

The composite stretchable member according to a fourth aspect of the present invention has a heat retaining rate HR of 40% or less. The composite stretchable member according to the fourth aspect of the present invention preferably further has a thickness t of 2.0 mm or less.

The composite stretchable member according to a fifth aspect of the present invention has density D of 8 to 15/cm. The composite stretchable member according to the fifth aspect of the present invention preferably further has a root mean square height Pq of 0.4 mm or less.

The composite stretchable member according to a sixth aspect of the present invention has a mean compressive pressure, when compressing the composite stretchable member in the thickness direction so that the load which is applied to the composite stretchable member in a 50% stretched state changes from 0.5 gf/cm$^2$ to 50 gf/cm$^2$, of less than 15 gf/cm$^2$ and has a root mean square height of a profile curve in a 50% stretched state of 0.4 mm or less.

The composite stretchable member according to the sixth aspect of the present invention preferably further has thickness t, when applying 3 gf/cm$^2$ (0.3 kPa) of pressure to the composite stretchable member in a 50% stretched state in the thickness direction, of 2.0 mm or less.

The composite stretchable member according to the sixth aspect of the present invention preferably further has a coefficient of variation CV of length of the profile curve elements in a 50% stretched state of 0.2 or less.

The composite stretchable member according to the sixth aspect of the present invention preferably further has a heat retaining rate HR in a 50% stretched state of 40% or less.

The composite stretchable member according to the sixth aspect of the present invention preferably further has a density D of profile curve elements in a 50% stretched state of 8 to 15/cm.

EXAMPLES 1 to 9

Examples 1 to 9 were prepared according to Table 1. Examples 1 to 8 were provided with constitutions corresponding to the embodiment shown in FIG. 1 to FIG. 5, while Example 9 was provided with the constitution corresponding to the embodiment shown in FIG. 9.

TABLE 1

| Item | Ex. 1 | Ex. 2 | Ex. 3 | Ex. 4 | Ex. 5 | Ex. 6 | Ex. 7 | Ex. 8 | Ex. 9 | Comp. Ex. 1 | Comp. Ex. 2 |
|---|---|---|---|---|---|---|---|---|---|---|---|
| Shaping treatment | Yes | | | | | | | | | None | None |
| Fastening of nonwoven fabric sheets together | No | | | | | | | | | Emboss fastening at 8 mm pitch | None |
| Fastening of elastic members and nonwoven fabric sheets | Fastened by adhesive applied to elastic members (amount of adhesive: 0.02 g/m) | | | | | | | | | None | Fastened by adhesive applied to elastic members (amount of adhesive: 0.02 g/m) |
| Type of nonwoven fabric sheets | SMS | | | | Spun bond | | | | | Air-thru/ point bond | Spun bond |
| Basis weight of nonwoven fabric sheets (g/m²) | 11 | | | | 17 | | | | | Air-thru: 18 Point bond: 21 | 17 |
| Thickness of nonwoven fabric sheets (mm) | 0.13 | | | | 0.19 | | | | | Air-thru: 0.5 Point bond: 0.19 | 0.19 |
| Type of elastic members (dTEX) | Urethane elastic yarn: 470 | | | | | | | | | Urethane elastic yarn: 310 | Urethane elastic yarn: 470 |
| Pitch of elastic members (mm) | 5 | | | | | | | | | | |
| Stretch-bond ratio of elastic members (X) | 2.3 | 2.5 | 2.7 | 3.0 | 2.3 | 2.5 | 2.7 | 3.0 | 3.0 | 3.2 | 3.0 |
| Maximum extension ratio (X) | 2.20 | 2.33 | 2.47 | 2.53 | 2.05 | 2.17 | 2.24 | 2.53 | 2.63 | 3.04 | 2.72 |

COMPARATIVE EXAMPLE 1

Figure 13:
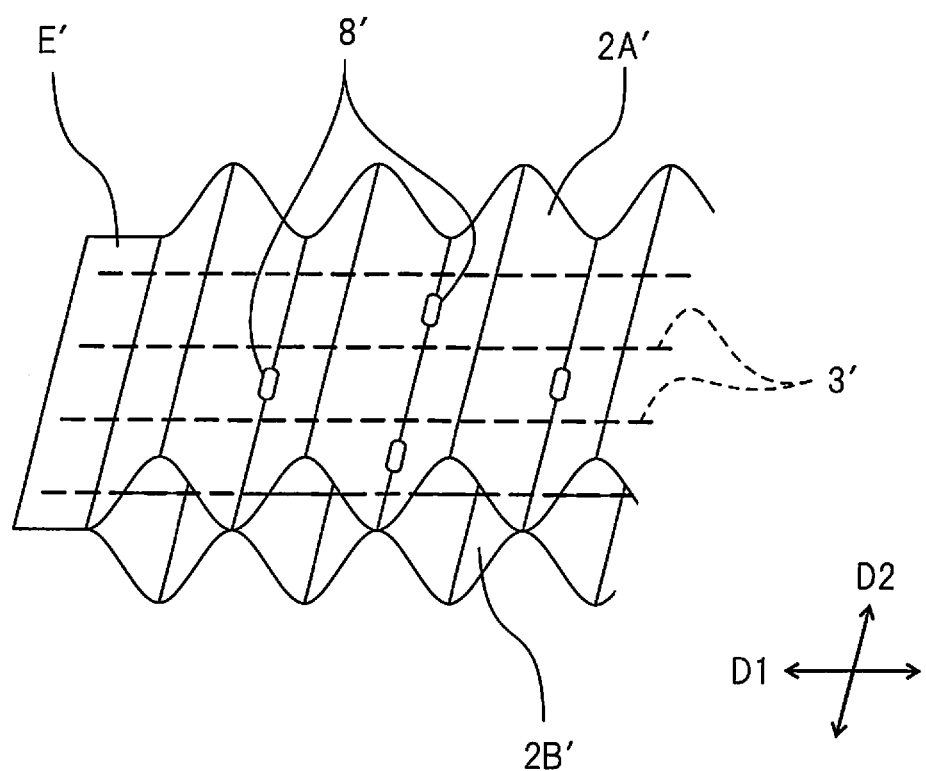
FIG. 13 is a perspective view of Comparative Example 1.
Figure 14:
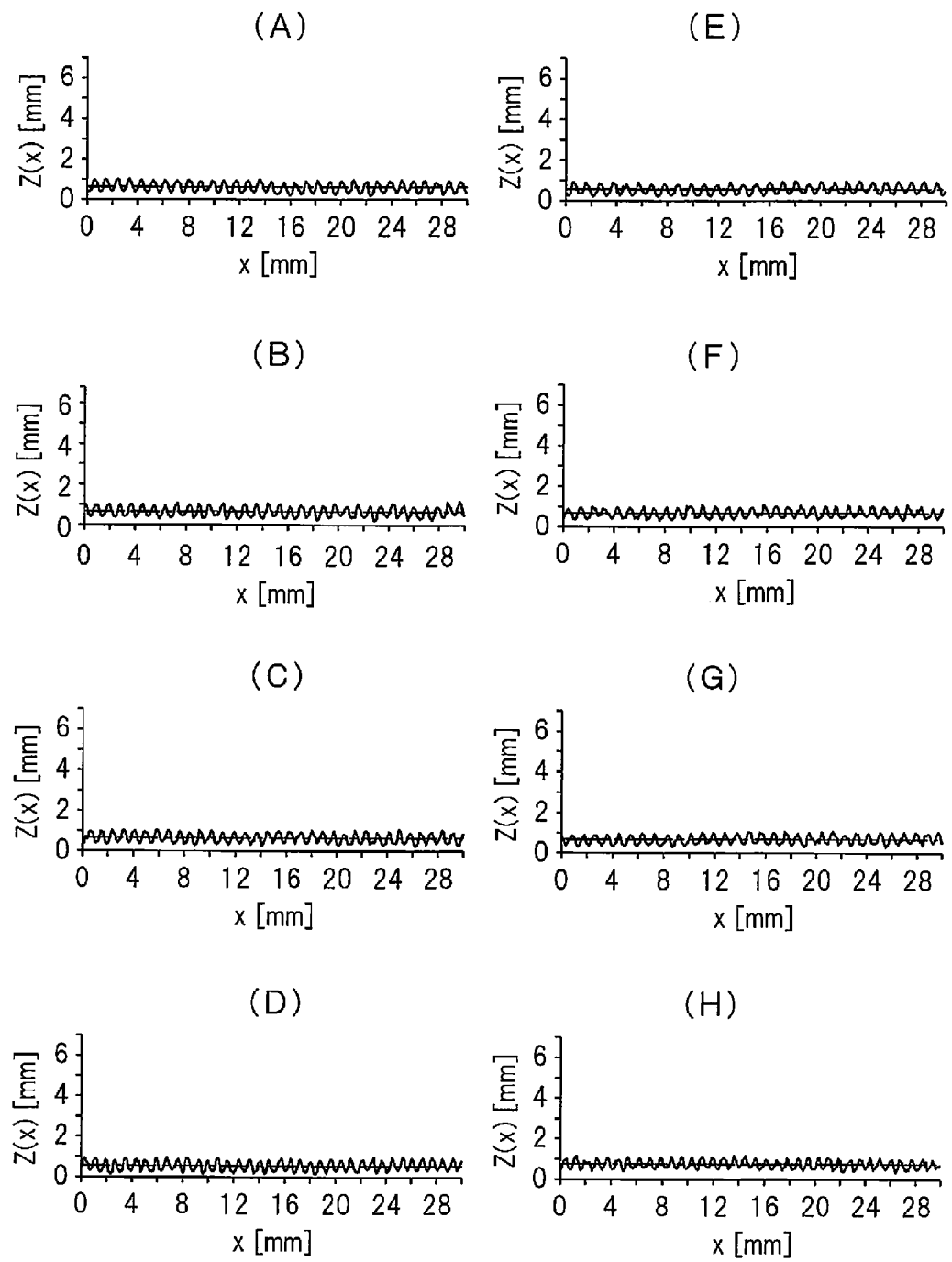
FIGS. 14A-H are graphs which show measurement results.
Figure 15:
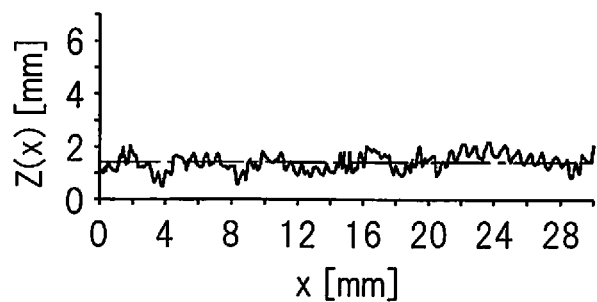
FIG. 15 is a graph which shows measurement results.

Comparative Example 1 was prepared according to Table 1. Comparative Example 1 was provided with a constitution corresponding to the composite stretchable member which is described in the above-mentioned PTL 1. That is, Comparative Example 1, as shown in FIG. 13, was provided with a mutually superposed, unshaped first nonwoven sheet part 2A' and second nonwoven sheet part 2B' and a plurality of elastic members 3' which is arranged between the first nonwoven sheet part 2A' and the second nonwoven sheet part 2B'. The first nonwoven sheet part 2A' and the second nonwoven sheet part 2B' were joined together at joined parts 8' which are provided discontinuously in the first direction D1 and in the second direction D2 which is perpendicular to the first direction. The elastic members 3' extended in the first direction D1 while separated from each other in the second direction D2 without passing through the joined parts 8', and were fastened to the first nonwoven sheet part 2A' and the second nonwoven sheet part 2B' at the two ends E' of the composite stretchable member in the first direction.

COMPARATIVE EXAMPLE 2

Comparative Example 2 was prepared in accordance with Table 1. Comparative Example 2 was provided with a mutually superposed, unshaped first nonwoven sheet part and the second nonwoven sheet part and a plurality of elastic members which are arranged between the first nonwoven sheet part and the second nonwoven sheet part. Adhesive was applied to the circumferential surfaces of the elastic members, so the first nonwoven sheet part and the second nonwoven sheet part were fastened with each other through the elastic members.

(Measurement)

The thickness t was measured by a thickness measuring device FS-60DS made by Daiei Kagaku Seiki Manufacturing. The area of the pressing plate was 20 cm² (circular shape), while the measurement load was 3 gf/cm² (0.3 kPa). A sample of the composite stretchable member (width 120 mm, length 1000 mm) was measured 10 times. The arithmetic mean of the measured data was found whereby the thickness t was obtained.

The profile curve was measured by a shape measuring system KS-1100, a laser sensor LK-G30 (spot diameter 30 μm), and a controller LK-GD500 made by Keyence Co., Ltd. The measurement range was 0 to 30000 μm, the measurement pitch was 5 μm, the number of measurement points was 6001, the contact probe movement direction was made the stretching direction, and the contact probe movement speed was 50 μm/sec. Later explained test pieces were prepared from the sample (width 120 mm, length 200 mm). Next, the test pieces were measured. A ±12 moving average was taken once, whereby profile curve data was obtained. Further, from the profile curve data, the root mean square height Pq, arithmetic mean PSm of the length Xs, standard deviation σ and coefficient of variation CV of the profile curve elements, and the density D of profile curve elements were calculated.

Figure 12:
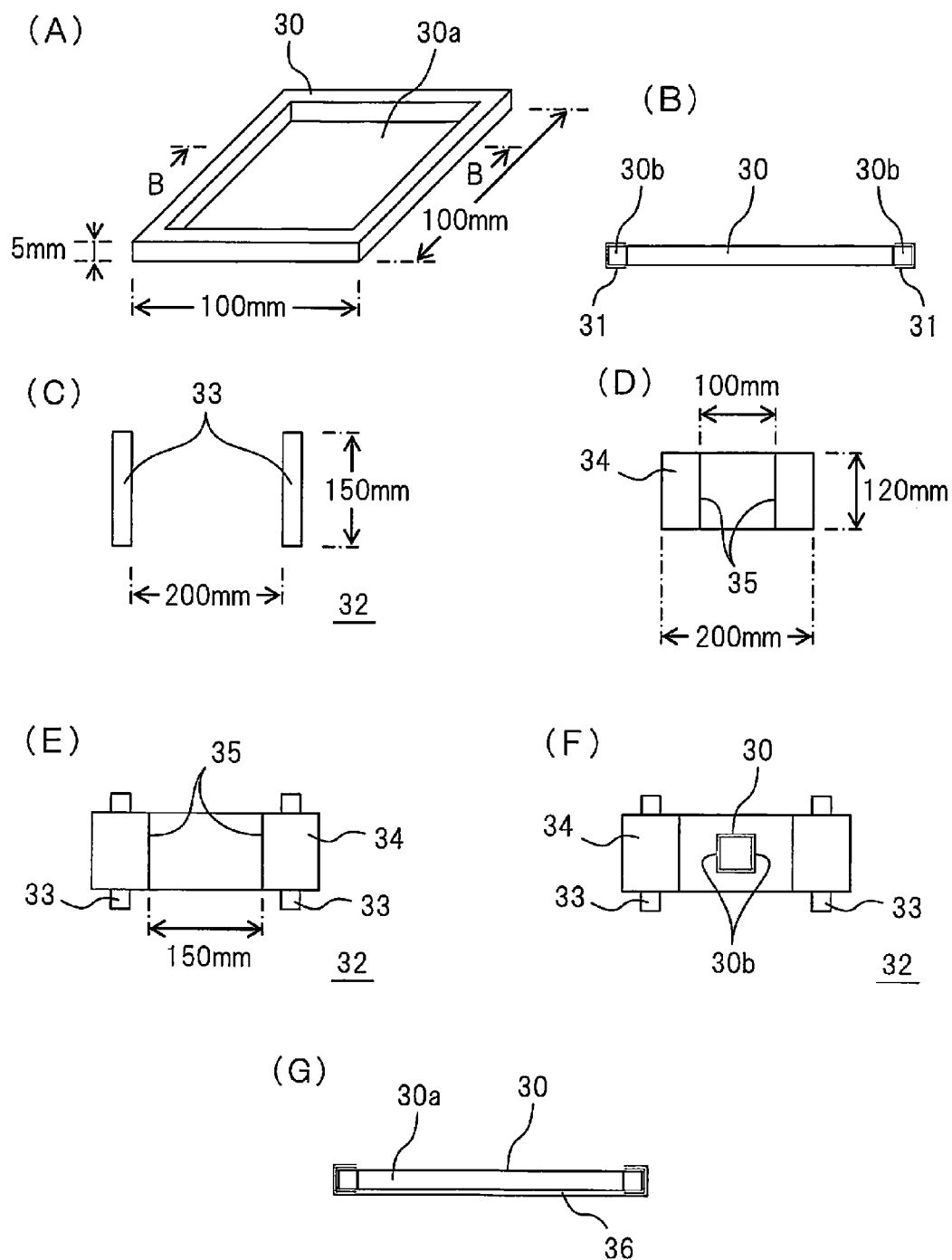
FIGS. 12A-G are views which explain a routine for preparing a test piece.

The test pieces were prepared as follows: That is, as shown in FIG. 12(A), a square shaped fastening fixture 30 having an opening 30a was prepared. As shown in the cross-sectional view along the line B-B of FIG. 12(A), that is, FIG. 12(B), hook tapes 31 were attached to two facing sides 30b of the fastening fixture 30. Further, as shown in FIG. 12(C), a pair of hook tapes 33 were attached to a table 32 at a 200 mm interval. Furthermore, as shown in FIG. 12(D), a sample 34 of the composite stretchable member (width 120 mm, length 200 mm) was prepared, and marks 35 were made in the stretching direction at a 100 mm interval on the sample 34.

Next, as shown in FIG. 12(E), the sample 34 was evenly stretched in the stretching direction so that the interval between the marks 35 became 150 mm, then was adhered to the hook tapes 33 on the table 32. Next, as shown in FIG. 12(F), the fastening fixture 30 was arranged on the sample 34 so that the two sides 30b became perpendicular to the stretch direction of the sample 34 and the sample 34 was adhered to the hook tapes 31. Next, the sample 34 was peeled off from the hook tapes 33 on the table 32, and the sample 34 was attached to the hook tapes 31 so as to be wrapped around the two sides 30b of the fastening fixture 30. Next, the parts of the sample 34 sticking out from the fastening fixture 30 were removed. As a result, a test piece 36 as shown in FIG. 12(G) was formed. The test piece 36 was measured for the composite stretchable member which is positioned at the opening 30a of the fastening fixture 30.

The mean compressive pressure PC was measured by an automatic compression tester KES-FB3-AUTO-A made by KATO TECH Co., Ltd. The compression distance was from a thickness T0 to a thickness Tm, the area of the pressing plate was 2 cm² (circular shape), the compression speed was 0.02 mm/sec, and the amp setting was SENS2. A test piece was prepared from the sample (width 120 mm, length 200 mm) (see FIG. 12(A) to FIG. 12(G)). Next, the test piece was measured three times. The arithmetic mean of the measured data was found whereby the mean compressive pressure PC was obtained.

The heat retaining rate HR was measured by a precise and fast thermal property measuring instrument KES-F7-Thermo Lab II made by KATO TECH Co., Ltd. The hot plate had dimensions of 10 cm by 10 cm. A test piece was prepared from the sample (width 120 mm, length 200 mm) (see FIG. 12(A) to FIG. 12(G)). Next, the test piece was measured three times. The arithmetic mean of the measured data was found and the heat retaining rate HR was obtained.

(Results)
Table 2 shows the measurement results.

From these, in Examples 1 to 9, it is learned that compared with Comparative Examples 1 and 2, the pleats are smaller and more uniform.

Figure 17:
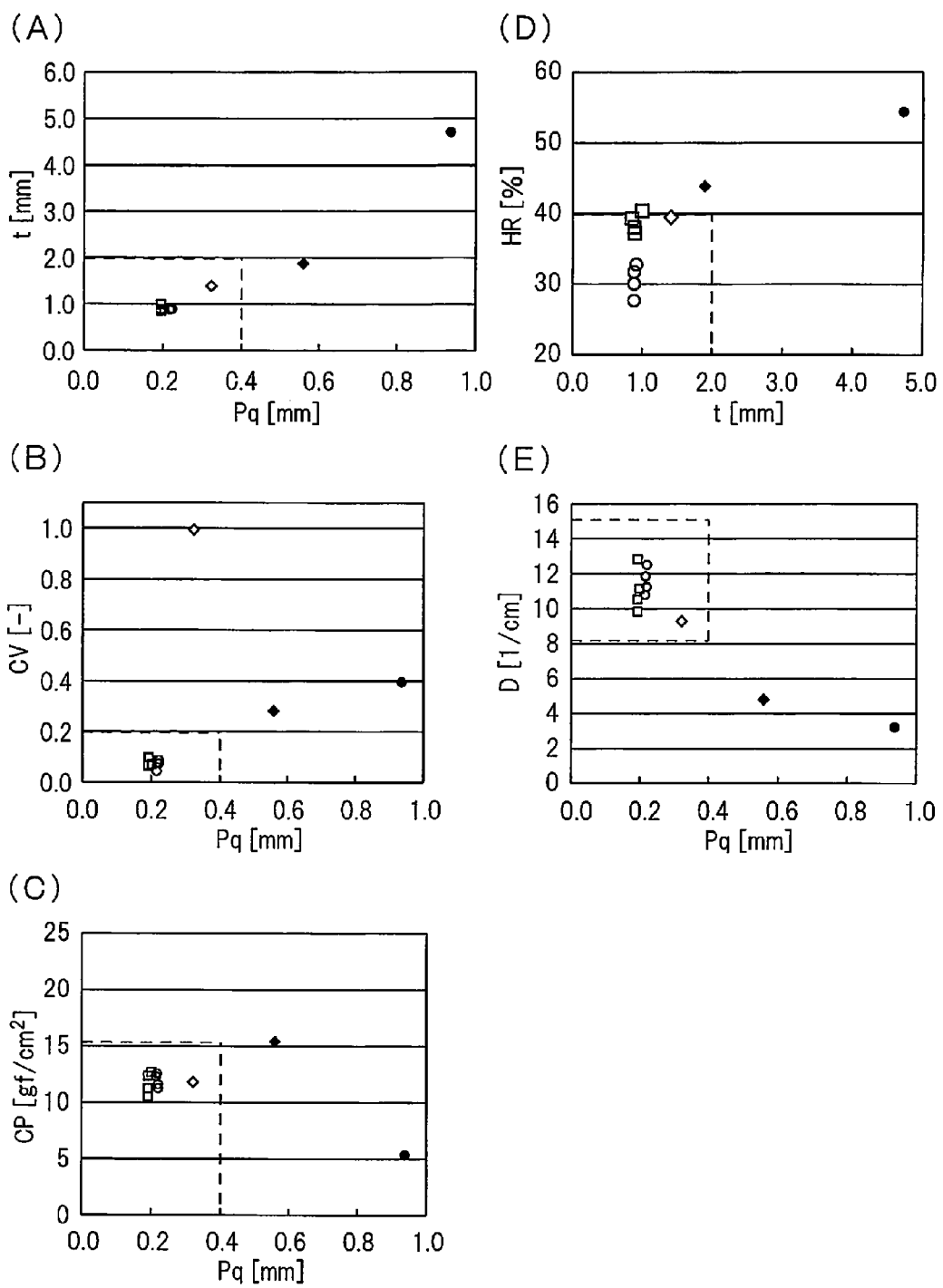
FIGS. 17A-E are graphs which show measurement results.

Further, as shown in FIG. 17(A), Examples 1 to 9 are in the range defined by Pq≤0.4 (mm) and t≤2.0 (mm). As opposed to this, Comparative Examples 1 and 2 were outside that range.

Furthermore, as shown in FIG. 17(B), Examples 1 to 8 were inside the range defined by Pq≤0.4 (mm) and CV ≤0.2. As opposed to this, Comparative Examples 1 and 2 were outside that range.

Furthermore, as shown in FIG. 17(C), Examples 1 to 9 were inside the range defined by Pq≤0.4 (mm) and CP<15 (gf/cm²). As opposed to this, Comparative Examples 1 and 2 were outside that range.

Furthermore, as shown in FIG. 17(D), Examples 1 to 9 were inside the range defined by t≤2.0 (mm) and HR≤40(%). As opposed to this, Comparative Examples 1 and 2 were outside that range.

Furthermore, as shown in FIG. 17(E), Examples 1 to 9 were inside the range of Pq≤0.4 (mm) and 8≤D (1/cm)≤15. As opposed to this, Comparative Examples 1 and 2 were outside that range.

The present invention is defined as follows.

(1) A composite stretchable member which can stretch in a first direction, comprising
a first nonwoven sheet part and a second nonwoven sheet part which are superposed each other and
a plurality of elastic members which are arranged between the first nonwoven sheet part and the second nonwoven sheet part;

TABLE 2

| Item | Ex. 1 | Ex. 2 | Ex. 3 | Ex. 4 | Ex. 5 | Ex. 6 | Ex. 7 | Ex. 8 | Ex. 9 | Comp. Ex. 1 | Comp. Ex. 2 |
|---|---|---|---|---|---|---|---|---|---|---|---|
| t (mm) | 0.89 | 0.89 | 0.89 | 0.92 | 0.86 | 0.89 | 0.90 | 1.00 | 1.41 | 4.72 | 1.89 |
| Pq (mm) | 0.22 | 0.22 | 0.22 | 0.22 | 0.20 | 0.20 | 0.20 | 0.20 | 0.32 | 0.94 | 0.56 |
| PSm (mm) | 0.93 | 0.90 | 0.85 | 0.80 | 1.02 | 0.96 | 0.90 | 0.78 | 1.08 | 3.08 | 2.09 |
| σ (mm) | 0.04 | 0.08 | 0.07 | 0.06 | 0.07 | 0.09 | 0.06 | 0.05 | 1.07 | 1.23 | 0.59 |
| CV (—) | 0.04 | 0.09 | 0.08 | 0.07 | 0.06 | 0.10 | 0.07 | 0.07 | 0.99 | 0.40 | 0.28 |
| D (1/cm) | 10.7 | 11.2 | 11.8 | 12.4 | 9.8 | 10.5 | 11.1 | 12.8 | 9.25 | 3.2 | 4.8 |
| WC (gf · cm/cm²) | 0.346 | 0.332 | 0.411 | 0.388 | 0.26 | 0.344 | 0.305 | 0.376 | 0.551 | 1.96 | 1.21 |
| Tm (mm) | 1.08 | 1.08 | 1.16 | 1.18 | 0.99 | 1.09 | 1.11 | 1.18 | 1.43 | 5.70 | 2.15 |
| T0 (mm) | 0.80 | 0.80 | 0.83 | 0.83 | 0.75 | 0.79 | 0.86 | 0.87 | 0.95 | 2.11 | 1.37 |
| T0 − Tm (mm) | 0.28 | 0.29 | 0.33 | 0.35 | 0.25 | 0.31 | 0.24 | 0.31 | 0.48 | 3.59 | 0.78 |
| CP (gf/cm²) | 12.2 | 11.5 | 12.5 | 11.2 | 10.5 | 11.2 | 12.6 | 12.3 | 11.6 | 5.5 | 15.4 |
| HR (%) | 30.1 | 27.6 | 31.7 | 32.8 | 39.2 | 38.0 | 37.2 | 40.3 | 39.5 | 54.5 | 43.9 |

Figure 16:
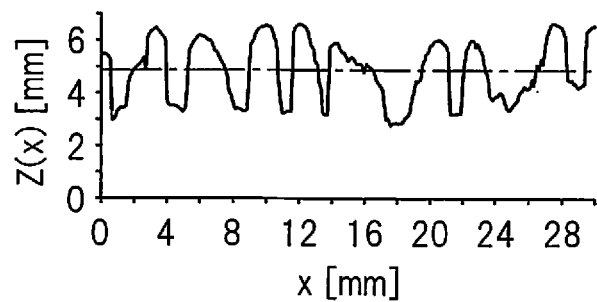
FIGS. 16A-B are graphs which show measurement results.
Figure 16:
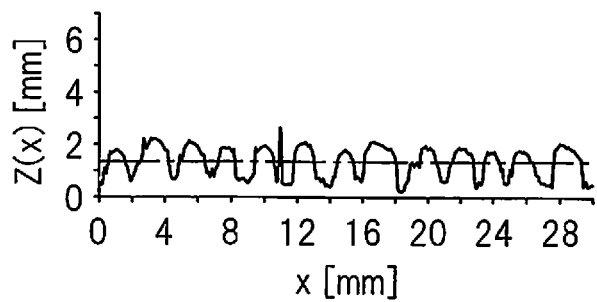

Further, FIGS. 14(A), 14(B), 14(C), 14(D), 14(E), 14(F), 14(G), 14(H), and 15 respectively show profile curves of Examples 1, 2, 3, 4, 5, 6, 7, 8, and 9. FIGS. 16(A) and 16(B) respectively show profile curves of Comparative Examples 1 and 2.

Furthermore, FIG. 17(A) shows the relationship between the root mean square height Pq and thickness t, FIG. 17(B) shows the relationship between the root mean square height Pq and the coefficient of variation CV, FIG. 17(C) shows the relationship between the root mean square height Pq and the mean compressive pressure CP, FIG. 17(D) shows the relationship between the thickness t and the heat retaining rate HR, and FIG. 17(E) shows the relationship between the root mean square height Pq and the density of the profile curve elements D. Note that, in FIG. 17(A) to FIG. 17(E), the white circles indicate Examples 1 to 4, the white squares indicate Examples 5 to 8, the white diamond indicates Example 9, the black circle indicates Comparative Example 1, and the black diamond indicates Comparative Example 2.

the elastic members extending in the first direction while being separated from each other in a second direction which is perpendicular to the first direction, the first nonwoven sheet part and the second nonwoven sheet part joined with each other by an adhesive which is applied to the elastic members.

(2) The composite stretchable member according to (1), wherein
a thickness when applying 3 gf/cm² of pressure in the thickness direction to the composite stretchable member in a 50% stretched state is 2.0 mm or less, and
a root mean square height of a profile curve in a 50% stretched state is 0.4 mm or less.

(3) The composite stretchable member according to (2), wherein a coefficient of variation of length of profile curve elements in a 50% stretched state is 0.2 or less.

(4) The composite stretchable member according to (2) or (3), wherein a mean compressive pressure when compressing the composite stretchable member in the thickness direction so that the load which is applied to the composite stretchable member in a 50% stretched state changes from 0.5 gf/cm² to 50 gf/cm² is less than 15 gf/cm².

(5) The composite stretchable member according to any one of (2) to (4), wherein a heat retaining rate in a 50% stretched state is 40% or less.

(6) The composite stretchable member according to any one of (2) to (5), wherein a density of profile curve elements in a 50% stretched state is 8 to 15/cm.

(7) The composite stretchable member according to (1), wherein a coefficient of variation of length of profile curve elements in a 50% stretched state is 0.2 or less.

(8) The composite stretchable member according to (1), wherein a heat retaining rate in a 50% stretched state is 40% or less.

(9) The composite stretchable member according to (1), wherein a density of profile curve elements in a 50% stretched state is 8 to 15/cm.

(10) The composite stretchable member according to any one of (2) to (9), wherein
the first nonwoven sheet part and the second nonwoven sheet part are respectively provided with
a plurality of convex-concave regions which are provided with convex parts and concave parts which are alternately repeated along the first direction and continue in the second direction and
at least one non-shaped region which separates these convex-concave regions from each other in the second direction,
the convex parts respectively stick out from the non-shaped regions in the thickness direction, and
the concave parts respectively reach the non-shaped regions between two mutually adjoining convex parts.

(11) The composite stretchable member according to (10), wherein
the first nonwoven sheet part and the second nonwoven sheet part are superposed so that the convex-concave regions adjoin each other and the non-shaped regions are separated from each other and so that the convex-concave regions are aligned with each other and the non-shaped regions are aligned with each other in the second direction, and
the elastic members are arranged between the mutually aligned non-shaped regions.

(12) The composite stretchable member according to (1), wherein
a mean compressive pressure when compressing the composite stretchable member in the thickness direction so that the load which is applied to the composite stretchable member in a 50% stretched state changes from 0.5 gf/cm² to 50 gf/cm² is less than 15 gf/cm², and a root mean square height of a profile curve in a 50% stretched state is 0.4 mm or less.

(13) The composite stretchable member according to (12), wherein a coefficient of variation of length of profile curve elements in a 50% stretched state is 0.2 or less.

(14) The composite stretchable member according to (12) or (13), wherein a heat retaining rate in a 50% stretched state is 40% or less.

(15) The composite stretchable member according to any one of (12) to (14), wherein a density of profile curve elements in a 50% stretched state is 8 to 15/cm.

(16) The composite stretchable member according to any one of (12) to (15), wherein
the first nonwoven sheet part and the second nonwoven sheet part are respectively provided with
a plurality of convex-concave regions which are provided with convex parts and concave parts which are alternately repeated along the first direction and which continue in the second direction and
at least one non-shaped region which separates these convex-concave regions from each other in the second direction,
the convex parts respectively stick out from the non-shaped regions in the thickness direction, and the concave parts respectively reach the non-shaped regions between two mutually adjoining convex parts.

(17) The composite stretchable member according to (16), wherein
the first nonwoven sheet part and the second nonwoven sheet part are superposed so that the convex-concave regions adjoin each other and the non-shaped regions are separated from each other and so that the convex-concave regions are aligned with each other and the non-shaped regions are aligned with each other in the second direction, and
the elastic members are arranged between the mutually aligned non-shaped regions.

The invention claimed is:

1. A composite stretchable member which is stretchable in a first direction, said composite stretchable member comprising:
    a first nonwoven sheet part and a second nonwoven sheet part which are superposed over each other; and
    a plurality of elastic members which are arranged between the first nonwoven sheet part and the second nonwoven sheet part,
    wherein
    the elastic members extend in the first direction while being separated from each other in a second direction which is perpendicular to the first direction,
    the first nonwoven sheet part and the second nonwoven sheet part are joined with each other by an adhesive which is applied to the elastic members,
    a thickness of the composite stretchable member, when applying 3 gf/cm² of pressure in a thickness direction of the composite stretchable member to the composite stretchable member in a 50% stretched state, is 2.0 mm or less, and
    a root mean square height of a profile curve of the composite stretchable member in the 50% stretched state is 0.4 mm or less.

2. The composite stretchable member according to claim 1, wherein a coefficient of variation of length of profile curve elements of the composite stretchable member in the 50% stretched state is 0.2 or less.

3. The composite stretchable member according to claim 1, wherein a mean compressive pressure, when compressing the composite stretchable member in the thickness direction so that a load which is applied to the composite stretchable member in the 50% stretched state changes from 0.5 gf/cm² to 50 gf/cm², is less than 15 gf/cm².

4. The composite stretchable member according to claim 1, wherein a heat retaining rate of the composite stretchable member in the 50% stretched state is 40% or less.

5. The composite stretchable member according to claim 1, wherein a density of profile curve elements of the composite stretchable member in the 50% stretched state is 8 to 15/cm.

6. The composite stretchable member according to claim 1, wherein
the first nonwoven sheet part and the second nonwoven sheet part are respectively provided with
a plurality of convex-concave regions provided with convex parts and concave parts which are alternately repeated along the first direction and continue in the second direction; and
at least one non-shaped region which separates the convex-concave regions from each other in the second direction,
the convex parts respectively stick out from the non-shaped regions in the thickness direction, and
the concave parts respectively reach the non-shaped regions between two mutually adjoining convex parts.

7. The composite stretchable member according to claim 6, wherein
the first nonwoven sheet part and the second nonwoven sheet part are superposed so that the convex-concave regions adjoin each other and the non-shaped regions are separated from each other and so that the convex-concave regions are aligned with each other and the non-shaped regions are aligned with each other in the second direction, and
the elastic members are arranged between the mutually aligned non-shaped regions.

8. A composite stretchable member which is stretchable in a first direction, said composite stretchable member comprising:
a first nonwoven sheet part and a second nonwoven sheet part which are superposed over each other; and
a plurality of elastic members which are arranged between the first nonwoven sheet part and the second nonwoven sheet part,
wherein
the elastic members extend in the first direction while being separated from each other in a second direction which is perpendicular to the first direction,
the first nonwoven sheet part and the second nonwoven sheet part are joined with each other by an adhesive which is applied to the elastic members, and
a coefficient of variation of length of profile curve elements of the composite stretchable member in a 50% stretched state is 0.2 or less.

9. A composite stretchable member which is stretchable in a first direction, said composite stretchable member comprising:
a first nonwoven sheet part and a second nonwoven sheet part which are superposed over each other; and
a plurality of elastic members which are arranged between the first nonwoven sheet part and the second nonwoven sheet part,
wherein
the elastic members extend in the first direction while being separated from each other in a second direction which is perpendicular to the first direction,
the first nonwoven sheet part and the second nonwoven sheet part are joined with each other by an adhesive which is applied to the elastic members, and
a heat retaining rate of the composite stretchable member in a 50% stretched state is 40% or less.

10. A composite stretchable member which is stretchable in a first direction, said composite stretchable member comprising:
a first nonwoven sheet part and a second nonwoven sheet part which are superposed over each other; and
a plurality of elastic members which are arranged between the first nonwoven sheet part and the second nonwoven sheet part,
wherein
the elastic members extend in the first direction while being separated from each other in a second direction which is perpendicular to the first direction,
the first nonwoven sheet part and the second nonwoven sheet part are joined with each other by an adhesive which is applied to the elastic members, and
a density of profile curve elements of the composite stretchable member in a 50% stretched state is 8 to 15/cm.

11. A composite stretchable member which is stretchable in a first direction, said composite stretchable member comprising:
a first nonwoven sheet part and a second nonwoven sheet part which are superposed over each other; and
a plurality of elastic members which are arranged between the first nonwoven sheet part and the second nonwoven sheet part,
wherein
the elastic members extend in the first direction while being separated from each other in a second direction which is perpendicular to the first direction,
the first nonwoven sheet part and the second nonwoven sheet part are joined with each other by an adhesive which is applied to the elastic members,
a mean compressive pressure, when compressing the composite stretchable member in a thickness direction of the composite stretchable member so that a load which is applied to the composite stretchable member in a 50% stretched state changes from 0.5 gf/cm$^2$ to 50 gf/cm$^2$, is less than 15 gf/cm$^2$, and
a root mean square height of a profile curve of the composite stretchable member in the 50% stretched state is 0.4 mm or less.

12. The composite stretchable member according to claim 11, wherein a coefficient of variation of length of profile curve elements of the composite stretchable member in the 50% stretched state is 0.2 or less.

13. The composite stretchable member according to claim 11, wherein a heat retaining rate of the composite stretchable member in the 50% stretched state is 40% or less.

14. The composite stretchable member according to claim 11, wherein a density of profile curve elements of the composite stretchable member in the 50% stretched state is 8 to 15/cm.

15. The composite stretchable member according to claim 11, wherein
the first nonwoven sheet part and the second nonwoven sheet part are respectively provided with
a plurality of convex-concave regions provided with convex parts and concave parts which are alternately repeated along the first direction and which continue in the second direction; and
at least one non-shaped region which separates the convex-concave regions from each other in the second direction,
the convex parts respectively stick out from the non-shaped regions in the thickness direction, and
the concave parts respectively reach the non-shaped regions between two mutually adjoining convex parts.

16. The composite stretchable member according to claim 15, wherein
the first nonwoven sheet part and the second nonwoven sheet part are superposed so that the convex-concave regions adjoin each other and the non-shaped regions are separated from each other and so that the convex-concave regions are aligned with each other and the non-shaped regions are aligned with each other in the second direction, and the elastic members are arranged between the mutually aligned non-shaped regions.

\* \* \* \* \*